US005561064A

United States Patent [19]
Marquet et al.

[11] Patent Number: 5,561,064
[45] Date of Patent: Oct. 1, 1996

[54] PRODUCTION OF PHARMACEUTICAL-GRADE PLASMID DNA

[75] Inventors: Magda Marquet, La Jolla; Nancy Horn, San Diego; Jennifer Meek, Encinitas; Gregg Budahazi, San Diego, all of Calif.

[73] Assignee: Vical Incorporated, San Diego, Calif.

[21] Appl. No.: 192,151

[22] Filed: Feb. 1, 1994

[51] Int. Cl.[6] .................................................. C12N 15/00
[52] U.S. Cl. ...................... 435/320.1; 435/91.1; 435/259
[58] Field of Search .............................. 435/172.1, 172.3, 435/320.1, 259, 91.1

[56] References Cited

U.S. PATENT DOCUMENTS

| | | | |
|---|---|---|---|
| 4,900,677 | 2/1990 | Hewitt | 435/259 |
| 4,923,978 | 5/1990 | McCormick | 536/25.41 |
| 4,935,342 | 6/1990 | Seligson et al. | 435/6 |
| 4,946,952 | 8/1990 | Kiefer | 536/25.4 |

FOREIGN PATENT DOCUMENTS

| | | |
|---|---|---|
| 0512767A1 | 11/1992 | European Pat. Off. |
| 0512768A1 | 11/1992 | European Pat. Off. |
| 0517515A2 | 12/1992 | European Pat. Off. |
| 92/13963 | 8/1992 | WIPO |

OTHER PUBLICATIONS

Sigma Chemical Company Catalog, 1993, pp. 224 and 325.
Current Protocols in Molecular Biology, Greene Publishing Assoc. & Wiley (1987). pp. 1.6.1–1.6.6 and 1.7.1–1.7.11.
Bolivar, et al., *Construction and Characterization of New Cloning Vehicles*, Gene 2:95–113 (1977).
Bywater, et al., *A Novel Chromatographic Procedure for Purification of Bacterial Plasmids*, Analytical Biochemistry 132:219–224 (1983).
Godson, et al., *A Simple Method of Preparing Large Amounts of ΦX174 RF I Supercoiled DNA*, Biochimica et Biophysica Acta 299:516–520 (1973).
Gorman, et al., *High Efficiency DNA–Mediated Transformation of Primate Cells*, Science 221:551–553 (1983).
Gorman, et al., *The Rous Sarcoma Virus Long Terminal Repeat is a Strong Promoter when Introduced into a Variety of Eukaryotic Cells by DNA–mediated Transfection*, Proc. Nat. Acad. Sci., USA 79:6777–6781 (1982).
Harding, et al., *Rapid Isolation of DNA from Complex Biological Samples Using a Novel Capture Reagent–Methidium–Spermine–Sepharose*, Nucleic Acids Research 17:6947–6958 (1989).
Hillen, et al., *Preparation of Milligram Amounts of 21 Deoxyribonucleic Acid Restriction Fragments*, Biochemistry 20:3748–3756 (1981).
Hines, et al., *Large–Scale Purification of Plasmid DNA by Anion–Exchange High–Performance Liquid Chromatography*, BioTechniques 12: 430–434 (1992).
Johnson, et al., *Large–Scale Isolation of Plasmid DNA and Purification of λ Phage DNA Using Hydroylapatite Chromatography*, Analytical Biochemistry 132:20–25 (1983).

Kozak, M., *An Analysis of 5'–Noncoding Sequences from 699 Vertebrate Messenger RNAs.*, Nucleic Acids Res. 15:8125–8148 (1987).
Mahon, et al., *Prenatal Lethality in a Transgenic Mouse Line is the Result of a Chromosomal Translocation*, Proc. Nat. Acad. Sci., USA 85:1165–1168 (1988).
Marko, et al., *A Procedure for the Large–Scale Isolation of Highly Purified Plasmid DNA Using Alkaline Extraction and Binding to Glass Powder*, Analytical Biochemistry 121:382–387 (1982).
McClung, et al., *Purification of Plasmid DNA by Fast Protein Liquid Chromatography on Superose 6 Preparative Grade*, Analytical Biochemistry 177:378–382 (1989).
Nabel, et al., *Direct Gene Transfer with DNA–Liposome Complexes in Melanoma: Expression, Biologic Activity, and Lack of Toxicity in Humans*, Proc. Nat. Acad. Sci., USA 90:11307–11311 (1993).
Overbeek, et al., *Tissue–Specific Expression in Transgenic Mice of a Fused Gene Containing RSV Terminal Sequences*, Science 231:1574–1577 (1986).
Raymond, et al, *Large–Scale Isolation of Covalently Closed Circular DNA Using Gel Filtration Chromatography*, Analytical Biochemistry 173:125–133 (1988).
Sambrook, et al., *Molecular Cloning, A Laboratory Manual*, Second Edition, Cold Spring Harbor Laboratory Press (1989). pp. 1.21–1.52.
Summerton, et al., *A Rapid Method for Preparation of Bacterial Plasmids*, Analytical Biochemistry 133:79–84 (1983).
Swanstrom, et al., *Nucleotide Sequence of Cloned Unintegrated Avian Sarcoma Virus DNA: Viral DNA Contains Direct and Inverted Repeats Similar to Those in Transposable Elements*, Proc. Nat. Acad. Sci., USA 78:124–128 (1981).
Thompson, *A Review of High–Performance Liquid Chromatography in Nucleic Acids Research. III. Isolation, Purification, and Analysis of supercoiled Plasmid DNA*, BioChromatography 1:68–80 (1986).

(List continued on next page.)

Primary Examiner—James Martinell
Attorney, Agent, or Firm—Knobbe, Martens, Olson & Bear

[57] ABSTRACT

The invention relates to a method for producing plasmid DNA, comprising the steps of: (a) lysing cells containing the plasmid DNA to obtain a lysate; (b) treating the lysate by a means for removing insoluble material to obtain a solute; and (c) applying the solute to differential PEG precipitations and chromatography to purify the plasmid DNA. In other embodiments of the invention, the plasmid DNA is produced with GRAS reagents; the plasmid DNA is produced in the absence of enzymes; the plasmid DNA is produced in the absence of organic extractants; the plasmid DNA is produced in the absence of mutagens; the lysing, treating and applying steps are scalable to result in the large scale manufacture of the plasmid DNA; and the lysing, treating and applying steps result in the generation of pharmaceutical grade material.

11 Claims, 1 Drawing Sheet

OTHER PUBLICATIONS

Thompson, et al., *Purification of Nucleic Acids by RPC–5 Analog Chromatography: Peristaltic and Gravity–Flor Applications,* Methods in Enzymology 100:368–399 (1983).

Westphal, et al., *Promoter Sequences of Murine α2(I) Collagen or of Avian Sarcoma Virus Genes Linked to the Bacterial Chloramphenicol Acetyl Transferase Gene Direct Tissue-specific Patterns of Chloramphenicol Acetyl Transferase Expression in Transgenic Mice,* Cold Spring Harbor Symp. Quant. Biol. 50:411–416 (1985).

Willis, et al., *Prep–A–Gene: A Superior Matrix for the Purification of DNA and DNA Fragments,* BioTechniques 9:92–99 (1990).

Yamada, et al., *A New Method for Extracting DNA or RNA for Polymerase Chain Reaction,* Journal of Virological Methods 27:203–210 (1990).

Mori, A., et al. (1985) Raid and economical method for purification of plasmid DNA. The Physico–Chemical Biology 29(4):41–45.

Horn, N., et al. (1995) Cancer gene therapy using plasmid DNA: purification of DNA for human clinical trials. Human Gene Therapy 6:565–573.

Lis, Methods Enzymol. 65: 347 (1980).

Field, Biotechniques 14: 532, 534, 536 (1993).

PRODUCTION OF PHARMACEUTICAL-GRADE PLASMID DNA

FIELD OF THE INVENTION

The invention relates to a method for producing plasmid DNA. The method is particularly concerned with a process for the isolation and purification of milligram, gram and kilogram quantities of pharmaceutical-grade plasmid DNA from recombinant cells. The method of the invention is useful in the field of gene therapy.

BACKGROUND OF THE INVENTION

A. Background

Provided herein is a new manufacturing process for the production of pharmaceutical grade DNA. Current state of the art techniques for the purification of plasmid DNA rely upon the use of laboratory scale centrifugation, extraction with toxic organic solvents, and the use of animal-derived enzymes (lysozyme, RNase, Proteinase K). Final purification of plasmid DNA from a lysate is accomplished using methods that may include laboratory scale ultra-centrifugation, preparative work gel electrophoresis, and research installation chromatography. None of these techniques are suitable for the large-scale manufacturing of pharmaceutical-grade plasmid DNA. The drawbacks of current techniques are described below.

Current laboratory methods are not amenable to manufacturing plasmid DNA. There are two widely used laboratory methods for the preparation of a crude lysate enriched with plasmid DNA: the boiling method and the alkaline lysis method. Both commonly utilize chicken egg-white lysozyme to break up the bacterial cell wall. Laboratory scale centrifugation is often implemented to separate cellular debris from the crude lysate. Pancreatic RNase is frequently employed to reduce host-derived RNA, which accounts for approximately 75% of the nucleic acid in the crude lysate. Organic extraction with phenol:chloroform:isoamyl alcohol or a variation of this mixture is typically used to reduce contaminating proteins. At this point the crude lysate still contains substantial contaminating host chromosomal DNA. Further treatment is necessary.

The method described above for obtaining a partially purified DNA from a crude lysate is not an optimal protocol for the manufacture of pharmaceutical grade DNA. Animal derived enzymes, such as lysozyme and RNase, present a problem. By virtue of being animal derived, they may introduce viral contamination into the final plasmid product. Organic solvents are also problematic. These chemicals are highly toxic and accordingly must be eliminated in the final dosage form if the product is intended to be a pharmaceutical. Moreover, the solvents add significant expense to the method in terms of not only storage, safe use and disposal of hazardous waste but also validation of their removal.

The plasmid DNA isolated from the crude lysate is further purified most often by cesium chloride/ethidium bromide (CsCl/EtBr) equilibrium ultra-centrifugation. Due to density differences created by the different binding capacities of EtBr to covalently closed circular plasmid DNA, RNA and chromosomal DNA, these three different nucleic acids can be resolved into enriched fractions by CsCl gradient ultra-centrifugation.

CsCl/EtBr gradient centrifugation is also undesirable as a method for the production of pharmaceutically acceptable DNA. It is not an economically scalable technique for the manufacture of DNA. Also, EtBr is a highly toxic, mutagenic and teratogenic reagent whose presence would not be tolerated, even at trace levels, in a pharmaceutical product and presents significant problems of safe disposal.

There are variations of the methodology described above where the crude lysate is treated with pancreatic RNase followed by an alkali/detergent treatment to reduce chromosomal DNA. An organic extraction with phenol:chloroform is followed by precipitation of DNA by ethanol, re-suspension and a polyethylene glycol (PEG) precipitation of DNA. Again, this is a time-consuming, laboratory-scale methodology not amenable to pharmaceutical manufacturing. It makes use of animal derived enzymes, toxic solvents and reagents not generally recognized as safe (GRAS) by the Food and Drug Administration (FDA).

The new process disclosed herein is suitable to manufacture pharmaceutical-grade DNA for such uses as gene therapy. This process is capable of separating various forms of plasmid DNA including supercoiled, relaxed and concatemers. The DNA produced by this manufacturing process is essentially free or contains only trace levels of host derived contaminants such as proteins, lipids, carbohydrates, endotoxins, chromosomal DNA, and RNA. It is manufactured using no animal- or otherwise-derived enzymes. The purification is accomplished using only reagents generally recognized as safe by the FDA. The manufacturing method of the invention is composed of a novel sequence of unit operations scalable to large quantities of DNA (milligrams, grams, kilograms) and is substantially more economical than current methods. Finally, the sequence of unit operations combined in this manufacturing process is complete including sterile fill of product DNA into appropriate vials. These attributes clearly distinguish the manufacturing process described here from current state of the art methods and make it especially well suited for the manufacture of pharmaceutical grade DNA.

B. Advantages.

There has been a significant effort devoted to developing alternative methods to CsCl/EtBr gradient ultra-centrifugation for the purification of DNA described above. These methods are all based on the replacement of the final ultra-centrifugation step by safer and more scalable methods. The object is to meet the same quality standards of the CsCl/EtBr gradient method. None of these methods, however, including the standard CsCl/EtBr method, achieves the quality standards of identity, purity, safety and potency required for a commercially licensed pharmaceutical drug.

The production of pharmaceutical grade proteins by recombinant technology has taught us that host contaminants (e.g., *E. coli* DNA, *E. coli* proteins, *E. coli* RNA, endotoxins) are reluctantly tolerated and vigorously regulated at trace levels in order for these proteins to become licensed pharmaceutical products. It has been learned from the production of standard pharmaceutical drugs that residues from processing reagents not generally recognized as safe must meet equally stringent standards.

The process, disclosed herein, for the production and purification of plasmid DNA meets all of the standards set by the FDA and like organizations in other countries for a pharmaceutical product derived from recombinant cells, such as *E. coli.*

The advantages of this method over existing state of the art methods is that it:

- is composed of scalable unit operations amenable to large scale manufacture;
- reliably removes host contaminants such as RNA, host DNA, proteins, lipopolysaccharides;
- does not rely upon the addition of extraneous animal derived proteins such as RNase, lysozyme, and Proteinase K;
- does not rely upon the use of toxic organic extractants;
- does not rely upon the use of mutagenic reagents such as ethidium bromide;
- uses only reagents generally recognized as safe by drug regulating bodies such as the FDA.

SUMMARY OF THE INVENTION

The invention relates to a process for the production and purification of plasmid DNA that meets all of the standards set by the FDA and like organizations in other countries for a pharmaceutical product derived from recombinant cells, including bacteria, such as *E. coli*, yeast, fungi, and mammalian and insect cells.

Previous DNA isolation methods are based on the replacement of the final centrifugation step by safer and more scalable methods, the objective being to meet the same quality standards of the CsCl/EtBr gradient method. None of these methods, however, including the standard CsCl/EtBr method, achieves the quality standards of identity, purity, safety and potency required for a commercially licensed pharmaceutical drug. The process invention described here takes the additional step to allow the production of a higher quality of DNA from cells all the way through a sterile fill to a finished product suitable for administration.

The novel combination of unit operations according to the invention results in a process significantly different from any process that has gone before. Disclosed herein is a process for the purification of plasmid DNA that:

- does not use any toxic or animal derived substance,
- is made of unit operations scalable to milligram, gram and kilogram quantities,
- is comprehensive in that it includes all steps from cell paste to final sterile fill, and
- meets quality criteria (identity, purity, potency) never achieved for previous plasmid purification methods but required for the licensing of a pharmaceutical product.

The advances achieved by this invention are of a substantially different intellectual thrust than any previous DNA isolation method.

According to the invention there is provided a method for producing plasmid DNA, comprising the steps of: (a) lysing cells containing the plasmid DNA to obtain a lysate; (b) treating the lysate by a means for removing insoluble material to obtain a solute; and (c) applying the solute to differential PEG precipitations and chromatography to purify the plasmid DNA.

In other embodiments of the invention, the plasmid DNA is produced with GRAS reagents; the plasmid DNA is produced in the absence of enzymes; the plasmid DNA is produced in the absence of organic extractants; the plasmid DNA is produced in the absence of mutagens; the lysing, treating and applying steps are scalable to result in the large scale manufacture of the plasmid DNA; and the lysing, treating and applying steps result in the generation of pharmaceutical grade material.

In yet another embodiment of the invention, the method further comprises the step of: (d) formulating, sterilizing and vial filling the plasmid DNA to yield a product suitable for therapeutic administration. The sterilization may comprise filtration.

According to another aspect of the invention, the cells are suspended in buffer and lysed in dilute base or dilute base and detergent. The buffer may be sodium acetate, the base sodium hydroxide and the detergent a nonionic surfactant. The cells may be suspended in a sodium acetate buffer to yield a homogeneous cell suspension and the cells may be lysed in a solution of sodium hydroxide and nonionic surfactant to yield a lysate. The lysate may be neutralized with an acid before subsequent treatment.

Based on still another aspect of the invention, the means for removing insoluble material comprises a filter.

In other embodiments of the invention, the differential PEG precipitations are followed by the chromatography; the differential PEG precipitations comprise a first precipitation with PEG to obtain a precipitate of impurities and a second precipitation with PEG to obtain a plasmid DNA precipitate; the first precipitation precedes the second precipitation; and the first precipitation comprises adding a PEG to a first plasmid DNA-containing solution to obtain a low PEG concentration, while the second precipitation comprises adding a PEG to a second plasmid DNA-containing solution to obtain a high PEG concentration.

In still other embodiments of the invention, the chromatography comprises ion exchange chromatography or gel filtration chromatography or a combination thereof; the gel filtration chromatography comprises allowing a plasmid-DNA-containing solution to contact with a size exclusion medium, having a DNA exclusion limit of about 20,000 base pair, at a pH of about 8.0 and a salt concentration of about 150 mM and recovering plasmid DNA-enriched fractions; and the ion exchange chromatography comprises allowing a plasmid DNA-containing solution to contact with an anion exchanger at a pH of about 8.0, developing a salt gradient between about 0.7M and about 0.9M, and recovering plasmid DNA-enriched fractions.

The invention also provides that step (b), may further comprise recovery from the solute, or a solution containing the plasmid DNA obtained from the solute, of a plasmid DNA precipitate by treatment with alcohol or PEG. Similarly, step (b), may further comprise removal from the solute, or a solution containing the plasmid DNA obtained from the solute, of a precipitate of impurities by treatment with high salt.

In another embodiment of the invention, the cells of are *E. coli* cells.

A pharmaceutically acceptable plasmid DNA prepared according to the process is also provided by the invention.

DETAILED DESCRIPTION OF THE INVENTION

Figure 1:
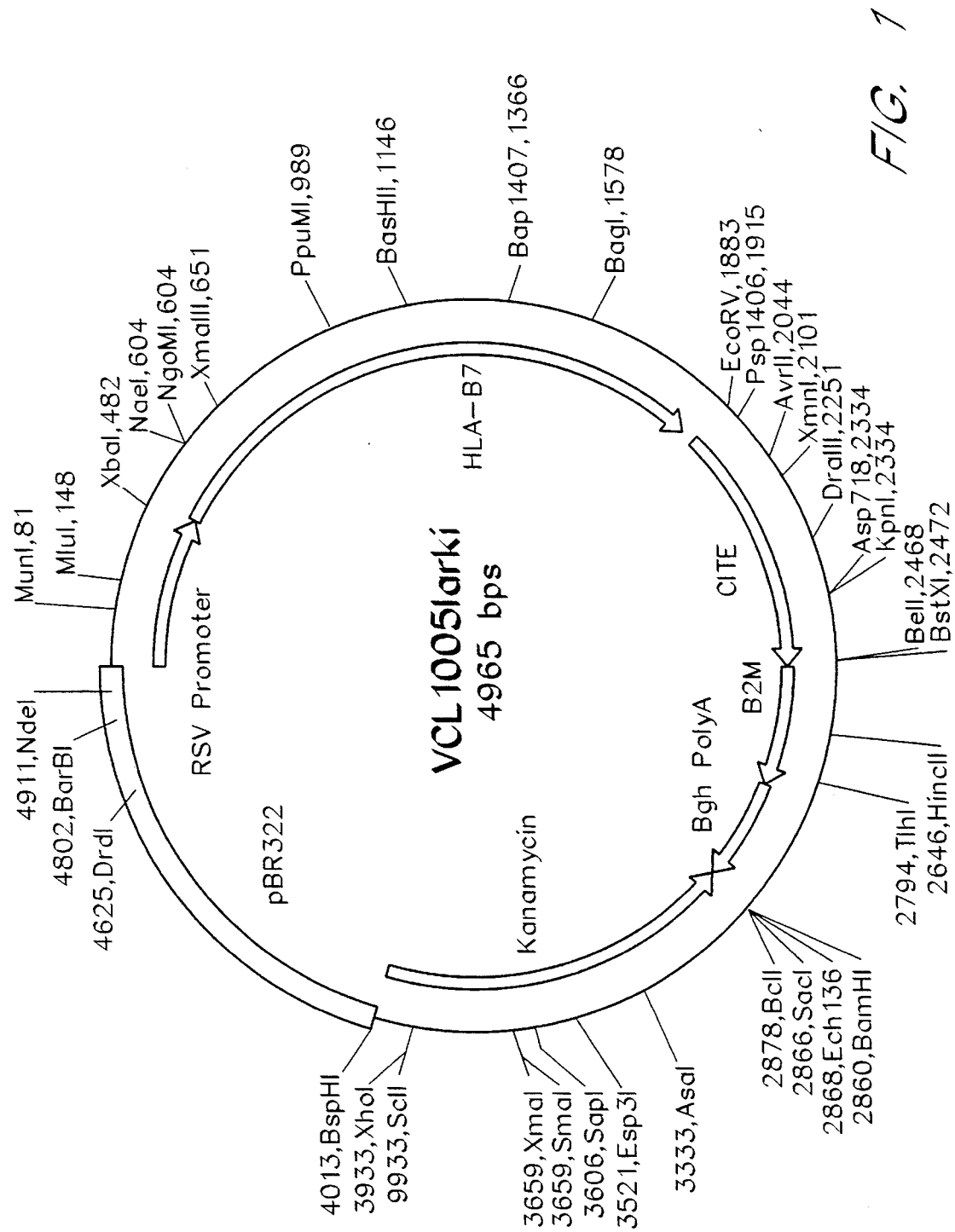
FIG. 1 is a plasmid map of VCL-1005.

The invention relates to a new process which is suitable to manufacture pharmaceutical grade DNA for such uses as gene therapy. This process replaces the standard CsCl/EtBr gradient method and yields a-higher quality product. It is capable of separating various forms of plasmid DNA sharing the same sequence including supercoiled, relaxed and concatemers. The DNA produced by this manufacturing process is essentially free of or contains only trace levels of host-derived contaminants. The purification is accomplished using only reagents generally recognized as safe (GRAS) by the FDA. The vialed product meets quality criteria (identity, purity, potency) never achieved for previous plasmid purification methods but required for the licensing of a pharmaceutical product.

This manufacturing process results in the production of milligram, gram and kilogram quantities of pharmaceutical grade plasmid DNA. In general, the method involves: lysing cells (e.g., bacteria, yeast, fungi, mammalian, insect or other cells) obtained through shake flask culture, bioreactor or fermentor propagation containing the plasmid DNA to obtain a crude lysate; concentrating and separating a partially purified DNA intermediate significantly enriched in plasmid DNA from host contaminants such as cell debris using filtration, centrifugation, any form of chromatography and/or differential precipitation methods; removing remaining contaminants such as proteins, RNA, lipids, and chromosomal DNA from the partially purified DNA intermediate by chromatography and/or differential precipitation methods; accomplishing a fine separation of residual contaminants and remaining forms of DNA by chromatography and/or differential precipitations; removing air-borne microbes introduced during processing by sterilizing the desired plasmid fraction, and aseptically filling vials for appropriate delivery of a pharmaceutical dosage form.

In this manufacturing process, the steps implement salts, buffers, solvents, extractants and precipitating agents that are generally recognized as safe by the FDA. Endotoxins/pyrogens are effectively separated from product to a level acceptable by the FDA. Host chromosomal DNA is separated from product DNA. Host proteins are isolated from product DNA. Different forms of DNA are segregated: supercoiled, relaxed and concatemers. The process is composed of scalable unit operations. It produces no hazardous organic waste products.

While purification of plasmid DNA using standard laboratory methods is frequently incomplete, leaving unacceptable levels of RNA, protein, endotoxins and host chromosomal DNA, the method of the invention is complete. Levels of host DNA, endotoxins/pyrogens, RNA and protein are reduced to undetectable or trace amounts.

The following chart compares standard laboratory methodology to one application of the manufacturing process described herein:

Following purification, the plasmid DNA is analyzed by Quality Control to ensure that it meets specifications. Following release by Quality Control, the DNA is formulated for sterile vial fill.

Standards Set by FDA and Like Organizations

Federal law requires that the use of pharmaceutical agents in the therapy of humans be approved by an agency of the Federal government. Responsibility for enforcement is the responsibility of the Food and Drug Administration (FDA), which issues appropriate regulations for securing such approval, detailed in 21 U.S.C. 301–392. Regulation for biologic material, comprising products made from the tissues of animals is provided under 42 U.S.C. 262. Similar approval is required by most foreign countries. Regulations vary from country to country, but the individual procedures are well known to those in the art.

Plasmid DNA

The plasmid DNA of the present invention is not limited. These plasmids are contemplated to include, for example, prokaryotic and eukaryotic vectors, cloning and expression vectors, pBR322 and pUC vectors and their derivatives, etc., and to incorporate various origins of replication, for instance, prokaryotic origins of replication, such as pMB1 and ColE1, and eukaryotic origins of replication, such as those facilitating replication in yeast, fungi, insect, and mammalian cells (e.g., SV40 ori) and also to encompass numerous genetic elements to facilitate cloning and expression, such as selectable genes, polylinkers, promoters, enhancers, leader peptide sequences, introns, polyadenylation signals, etc. The selection of vectors, origins, and genetic elements will vary based on requirements and is well within the skill of workers in this art. Similarly, a host can be chosen from among prokaryotes and eukaryotes, including bacterial, yeast, fungi, insect and mammalian cells. Preferred hosts are microbial cells, especially microorganisms like *E. coli*. Any suitable strain of *E. coli* is contemplated. Likewise, genes encoding diverse structural proteins (or peptides, polypeptides, glycoproteins, phosphoproteins, amidated proteins, etc.) may be inserted into the plasmid, which genes may constitute genomic DNA, cDNA, synthetic DNA, polynucleotide and oligonucleotide, etc. sequences. These sequences may be obtained using chemical synthesis or gene manipulation techniques (see Sambrook, Fritsch, Maniatis, *Molecular Cloning, A Laboratory Manual*, Second Edition, Cold Spring Harbor Laboratory Press, 1989; and *Current Protocols in Molecular Biology*,

| Procedure | Laboratory Method | Disclosed Pharmaceutical Manufacturing Process |
|---|---|---|
| 1. Cell Lysis | Employs Lysozyme, Tris, SDS | No Enzymes, Alternate Buffer such as Sodium Acetate, Alkaline pH and/or Tween ® 80 instead of SDS; only GRAS reagents used |
| 2. Removal of Cell Debris | Centrifugation | Filtration or Centrifugation |
| 3. Removal of Host Cell Derived Contaminants: RNA, Protein, Lipid, DNA | Uses Animal Derived Enzymes, Uses Organic Solvents | High Salt Precipitation, PEG Precipitation of Non-Plasmid Contaminants |
| 4. Plasmid Enriched Crude Lysate | Ethanol or Similar Alcohol | PEG Precipitation of Plasmid DNA |
| 5. Purification of Plasmid DNA | High-speed Centrifugation; CsCl/EtBr Gradients | Chromatography; Column is Scalable; No Toxic Reagents |

Greene Publishing Assoc. & Wiley, 1987, both of which are expressly incorporated by reference herein) and, further, may be inserted into plasmids and the plasmids subsequently introduced into host cells using additional gene manipulation techniques (id.). Turning to culturing of a plasmid DNA-containing host, this may be carried out using known processes such as those disclosed in the aforementioned references, and are contemplated as including incubator, bioreactor, fermentor etc., according to batch fermentation, fed batch fermentation, continuous culture, Type I, II and III fermentation, aseptic fermentation, consortium fermentation, protected fermentation, etc. Fitting the conditions (e.g., medium, temperature, pH, hours, agitation, aeration, etc.) for culture to the circumstances is empirical and well within the skill of those in the art.

In one application of the invention, pharmaceutical grade plasmid DNA is produced that is designed for the treatment of solid tumors in humans (VCL-1005). One clinical approach is to inject the tumor with a complex formulated in lactated Ringer's diluent of a cationic lipid mixture (e.g., DMRIE and DOPE) and a gene encoding a human major histocompatibility antigen (HLA-B7) (Nabel, Gary J., et al., Proc. Nat. Acad. Sci., U.S.A. 90:11307–11311 (1993)). This antigen is unique to specific individuals and is responsible for strong immune responses such as organ transplant rejection. The HLA-B7 gene codes for the production of the HLA-B7 protein. The expression of the protein is expected to trigger the body to produce a potent cytotoxic T lymphocyte response against the tumor cell. A description of VCL-1005 is provided in Example 1, an explanation of its construction is given in Example 2, and a characterization of a procedure for fermentation of VCL-1005 is presented in Example 3.

Cell Paste

After completion of the culturing of plasmid DNA-containing host cells, the recombinants are recovered in the usual way, e.g., by laboratory., pilot plant, or industrial scale centrifugation and/or filtration, depending on the specific application. The cells can be stored frozen, using standard methodology, or may be processed immediately.

Resuspend Cells in Buffer

The resultant cell paste is resuspended in buffer using resuspension techniques to resuspend the cells. The buffer is not limited. Preferably, it constitutes a reagent that is generally recognized as safe (GRAS) by the Food and Drug Administration (FDA). Such buffers include sodium acetate, potassium citrate, sodium phosphate monobasic or dibasic or a mixture, and the like, with sodium acetate being preferred. The selection of pH and ionic strength is well within the level of skill in the art.

Lyse Cells

In this step, the cells are lysed, using lysis techniques, to precipitate non-plasmid impurities such as chromosomal DNA, high molecular weight RNA, protein and membrane complexes. According to a preferred embodiment, the cells are lysed without resort to animal- or otherwise-derived enzymes, such as lysozyme. Advantageously, lysis is carried out in a dilute base or a dilute base and a detergent. Neither the base nor the detergent are limited. It is preferred that they represent GRAS reagents. Such bases are sodium hydroxide, potassium hydroxide, sodium bicarbonate, etc., while such detergents constitute pharmaceutically acceptable nonionic surfactants, e.g., polysorbates (sold under the trademark Tween®), polyoxyethylene ethers sold by Union Carbide (Triton®), and the like. A NaOH and Tween® combination is advantageous, with a Tween® 80 being preferred. Optimization of pH and ionic strength is well within the skill of the art. An alternative embodiment to alkaline lysis is mechanical breakage using, e.g., a French Press, a microfluidizer, and the like.

Acidify Lysate

Optionally, the lysate is acidified at this stage, using acidification techniques, to facilitate subsequent removal of insoluble material resulting from cell lysis by reducing the viscosity created during alkaline treatment. Any acid may be employed. Preferably it is a GRAS ingredient, such as glacial acetic acid, phosphoric acid, citric acid, and the like. The matching of pH and ionic strength is empirical and well within the skill of workers in this art.

Remove Cell Debris and Other Impurities

In this step, the cell debris and high molecular weight impurities released during cell lysis are removed by laboratory, pilot plant or industrial scale centrifugation and/or filtration in the usual way. Filtration is advantageous to ensure a clarified lysate prior to the next positive precipitation. As is well-known to practitioners, filtration may be facilitated to enhance the flow properties of heterogeneous or viscous solutions by the employment of aids that include cellulose, siliceous earth, Celite® filtering aid, etc.

The material through which the lysate is filtered according to the method of the invention comprises apertures or pores having a diameter large enough to allow plasmid DNA to pass through with the filtrate but small enough so that the assembled filter retains a large proportion of the insoluble material. Pore sizes may be irregular and variable as long as the total effect is to retain the precipitate. Accordingly pore sizes are preferably from about 0.1 to 100 microns, with a range of from about 0.5 to 50 particularly preferred. The material from which the filter is manufactured can be a synthetic material or an organic or inorganic natural material; however, it should not be a naturally occurring organic plant or animal product that could contain contaminating nuclear material. The filter material is also advantageously autoclavable, malleable, and strong, and is capable of being assembled in layers to achieve various filtering efficiencies adaptable to unique experimental situations. It is preferably non-absorbent, and can be hydrophilic or hydrophobic; however, the hydrophobicity should not retard the flow of filtrate. Examples of suitable filter materials are glass, plastic, or metal screens, porous films, cellulose or fiber mats, woven or nonwoven fabrics, or a synthetic fabric, such as nylon or rayon, e.g., Miracloth® (Calbiochem, Cat.#475855, La Jolla, Calif.), a synthetic nonwoven rayon fabric having an average pore size of 22 to 25 μm. Although materials such as porous fritted glass disks can be used, the filter material is preferably flexible. The filtration can be performed under conditions of gravity, pressure or vacuum.

Precipitate Plasmid DNA from Clarified Filtrate

The procedure followed to obtain a plasmid DNA precipitate typically features lysing cells and harvesting plasmid DNA by way of alcohol precipitation, for example, using ethanol or isopropanol, and involves the variables of temperature, presence of monovalent cations, and centrifugation. This technique is adequate for small scale processing but becomes a problem when moving to large scale pharmaceutical manufacture of plasmid DNA. When using an alcohol as the precipitating agent, temperature needs to be closely controlled to achieve reproducible results. The maintenance of temperature to the extent necessary when alcohols are used in large volumes is expensive and difficult to engineer. Moreover, alcohols require explosion proof precipitation tanks and processing areas when used in process scale-ups (e.g., blow out walls, etc.). This requirement can dramatically increase the cost of building design and construction. It can also limit the zoning areas where such a facility may be located. Further, ethanol and 2-propanol must be disposed of as hazardous waste. This kind of waste disposal can be become expensive. It is an advantage to design a process that does not rely on using large volumes of alcohol.

Polyethylene glycols (PEGs) or other similar high molecular weight polyols may be used as precipitants and extractants in both protein and nucleic acid recovery. PEG precipitation is advantageous for the manufacture of DNA. It is an acceptable ingredient in pharmaceuticals. Unlike alcohol precipitants, temperature need not be closely monitored to achieve reproducible results. PEG's do not confer the problems that alcohols do, such as propensity to explode, nor do they accord hazardous waste difficulties.

For these reasons, optionally, the alcohol precipitation is replaced by a PEG precipitation. In this step, a PEG is added to the clarified filtrate to result in a high concentration of PEG. Bringing the final concentration to about 10% PEG (weight/volume) may be advantageous (supra). A PEG-8000 is favored. Application of standard precipitation techniques and selection of pH and ionic strength is well within the skill of those in the art.

Collect Partially Purified DNA

The precipitate of plasmid DNA that is formed as a consequence of alcohol or PEG precipitation is separated in the usual way by laboratory, pilot plant, or industrial scale centrifugation and/or filtration.

Filtration can be carried out on any filter material that meets the requirements of a pore size that is effective in recovering the plasmid DNA precipitate, while allowing efficient passage of solvent. Pore size in the filter may be variable as long as the filtration performance is effective. The most effective filter for this application depends on the size of the aggregated DNA to be filtered, and the aggregate size depends in turn on the precipitating agent and the solvent. Matching of filter, precipitate and solvent is empirical, and is within the skill of workers in this art. Effective filtration is determined by maximum recovery of product and minimum retention of contaminants on the filter. Suitable filters will have pore diameters or ranges of pore diameters from about 0.1 to 100 microns, preferably from about 0.1 to 50 microns. The filter material for this stage plasmid DNA filtration will preferably have the physical characteristics described above for the separation of cell debris, that is, made of synthetic or inorganic material, or material not contaminated with nuclear components, autoclavable, strong and malleable.

Dissolve Partially Purified DNA in Buffer and Precipitate RNA and Lipopolysaccharide Impurities with High Salt Here, as throughout the method of the invention, when the plasmid precipitate is resuspended in a buffer, resuspension techniques are used, and buffers that are GRAS buffering agents are preferably employed.

In this step, high salt precipitation may be performed, using precipitation techniques and selecting pH and ionic concentrations as will be known to those with skill in the art. A high salt precipitation is effective to remove some of the contaminating RNA and much of the lipopolysaccharides. The salt is unlimited, but is preferably a GRAS ingredient. Ammonium acetate, lithium chloride, sodium chloride, sodium acetate, etc., are useful, with ammonium acetate being preferred.

Remove Precipitated Impurities

The precipitate of impurities that is formed as a consequence of high salt precipitation is separated using standard techniques by laboratory, pilot plant or industrial scale centrifugation and/or filtration. Filtration can be carried out on any filter material that meets the requirements of a pore size that is effective to retain the precipitate of impurities, while allowing a plasmid-DNA filtrate to be recovered. Effective filtration is determined by maximum recovery of contaminants and minimum retention of plasmid on the filter, that is, optimal flow-through of product. Suitable filters will have pore diameters or ranges of pore diameters from about 0.1 to 100 microns, preferably from about 0.1 to 50 microns. The filter material for this stage filtration will preferably have the physical characteristics described above for filtration, i.e., made of synthetic or inorganic material, or material not contaminated with nuclear components, autoclavable, strong, and malleable.

Precipitate High Molecular Weight DNA and RNA Impurities with Low Concentrations of PEG It was learned that differential polyethylene glycol (PEG) precipitation could replace organic extraction and other disadvantageous purification schemes by maximizing recovery of plasmid DNA and minimizing retention of contaminants to produce a superior plasmid DNA intermediate. Example 7. Here is exemplified a titration that was conducted to determine the optimal percentages of PEG required to be effective in the differential precipitation strategy. Based on this exemplification, those with skill in the art can perform a similar titration to ascertain equally optimal percentages.

According to the invention, the differential precipitation approach using PEG is constituted by the sequential addition of PEG to plasmid DNA solution in different concentrations to achieve isolation of plasmid from contaminants and host-derived impurities. In succession, PEG is introduced to a plasmid containing solution in sufficiently low percentages to precipitate out contaminants and impurities or at sufficiently high percentages effective to bring down the plasmid DNA. A low concentration cut may precede a high concentration cut, or a high concentration cut may be antecedent to a low concentration cut, or a series of precipitations may be realized in the order of high percentage cut, low percentage cut, and high percentage cut.

Based on a preferred embodiment, an approximately 4% PEG cut (weight/volume) and an approximately 10% PEG cut (weight/volume) are executed. The 4% cut is a negative precipitation that pulls out impurities such as chromosomal DNA and RNA, while the 10% cut results in the precipitation of plasmid DNA in a highly purified state. It may be advantageous to begin with a low concentration PEG precipitation and to follow with a high percentage PEG precipitation, e.g., a 4% cut may precede a high concentration cut, but this determination will vary depending on the circumstances. A PEG-8000 is preferred. Thus, a PEG is added to a sample containing plasmid DNA (e.g., the above filtrate) sufficient to attain a final concentration of PEG to 4% (w/v). Implementing standard precipitation techniques and adjusting pH and ionic strength as will be appreciated by those with skill in the art, a negative precipitation is achieved in this manner.

Remove Precipitated Impurities

Precipitated impurities are removed in the usual way centrifugation and/or filtration as described supra for the removal of precipitated impurities.

Precipitate Plasmid DNA with High Concentrations of PEG

In accord with the differential PEG precipitation described above, PEG is added to a plasmid DNA sample in high concentrations sufficient to precipitate out plasmid away from soluble contaminants and impurities. It may be advantageous to introduce PEG to the filtrate that is obtained after executing a low concentration PEG cut. Thus, one may effect a 4% cut and follow it with a high concentration PEG cut. A 10% cut may prove beneficial. In this case, PEG is added to a sample to a final concentration of 10% (weight/volume). A PEG 8000 is preferred. Choice of pH and ionic strength and application of standard precipitation techniques will be apparent to practitioners in the art to execute this step successfully.

Recover Plasmid DNA

Plasmid DNA is collected in the usual manner by centrifugation or filtration as described supra for the collection of partially purified DNA.

Dissolve Plasmid DNA Pellet in Buffer

Plasmid DNA is dissolved in buffer, preferably a GRAS buffering agent, and prepared for final purification.

Upon being separated from many host contaminants, such as chromosomal DNA, RNA, lipopolysaccharide and protein, a sample is obtained that is rich in plasmid DNA and yet may harbor small RNA oligonucleotides, trace amounts of chromosomal DNA, protein, endotoxins and residues left over from processing. According to the invention, further purification may be effected as an independent step to rid product of remaining nucleic acids, macromolecules, small molecular forms and residuals, and, moreover, to isolate covalently closed circular DNA, i.e., supercoiled monomers, from nicked circular plasmids (relaxed monomers) and concatenated forms (supercoiled dimers, etc.). Towards this end, a chromatography step is performed. Differences in ionic charge, molecular size, and/or other characteristics are exploited to bring about purification of the desired plasmid DNA species. Chromatography is contemplated to encompass ion exchange chromatography, size exclusion chromatography, reversed phase chromatography, hydrophobicity interaction chromatography, affinity chromatography, and any like chromatography, and, also, any combination of these to bring about the final purification of plasmid DNA.

Size Exclusion Chromatography on Pharmacia S-1000 Removes Remaining Impurities (Higher Molecular Weight Forms of DNA, RNA, Protein and Endotoxins)

Size exclusion is a simple and reproducible chromatographic method. It was found to be a superior method for the purification of plasmid DNA, by virtue of being capable of separating with precision and reproducibility contaminating RNA, chromosomal DNA, protein and endotoxins and, also, various plasmid DNA species. Example 8. Size exclusion, also known as gel filtration (and steric exclusion), consequently embodies a preferred embodiment of the chromatography step.

A product plasmid of interest will have a molecular weight that is on the order of the molecular weight of VCL-1005, that is, $3\times10^6$ kD, and even though this plasmid is about 5 kb in size, and while plasmids may be about half this size or 3, 4 or 5 times this size, the molecular weight of a plasmid will vary only by about a log. In contrast, endotoxins have an average molecular weight of 50,000 kD. Thus, it was hypothesized that product should readily separate from endotoxins on a size exclusion column. Also, agarose gel analysis showed that major problem contaminants were distinguishable from product mainly by differences in molecular weight. These characteristics combined to make size exclusion chromatography an attractive purification alternative.

Chromatographic purification of DNA presents a novel set of problems. The surface charge distribution on DNA is very different from that found on a protein. Proteins have domains with unique spatial-charge footprints that may be used with ion-exchange matrices to achieve high resolution separations. Yet, DNA has a uniform negatively charged surface without the distinctive domains common in proteins. Plasmid DNA, as suggested above, is also very large. Most commercially available ion exchange matrices have pore sizes in the 300–1000 Å range. Plasmid DNA requires at least 4000 Å pores. DNA binds well to large pore anion exchange matrices and RNA is readily separated from plasmid DNA with a simple salt gradient. However, endotoxins, plasmid concatemers and host cell DNA often smear across the plasmid peak. For these reasons, while anion exchange may be useful for the partial purification and/or concentration of plasmid DNA, and is contemplated as such, the method is limited by the commercially available matrices and the limitations inherent in the structure/charge of DNA.

The appeal of size exclusion chromatography is augmented by its usefulness as a final polishing step in processes designed to produce pharmaceuticals. Small molecular weight contaminants such as metals and salts are generally reliably removed to deliver a product with reproducible composition. It was for these reasons that the decision was made to explore size exclusion.

Pharmacia S-1000 (Pharmacia, Piscataway, N.J.) was chosen as the size exclusion medium because it is a commercially available matrice with molecular exclusion properties compatible with a very high molecular weight product. This resin is reported by Pharmacia to have a DNA exclusion limit of 20,000 base pair. Size exclusion chromatography using Pharmacia S-1000 was found to remove remaining impurities and distinguish various plasmid DNA species with superiority. Example 8. Thus, the gel filtration material is unlimited so long as it affords the separation of a very high molecular weight product, and, preferably, amounts to a Pharmacia S-1000 matrix or derivative, alternative or equivalent.

According to this step, then, the sample is loaded onto a chromatography column. The separation is generally run isocratically, that is, using a single mobile phase. Buffers for molecular separations constitute aqueous buffer in appropriate ionic concentration and pH as will be recognized by workers in this art. The sample volume should be an appropriate percentage of the column bed volume. Flow rates are maintained at suitable velocities. Chromatography is carried out using routine chromatographic techniques.

In another embodiment of the chromatography step, ion exchange chromatography is performed to separate plasmid DNA molecules from contaminating molecules based on molecular ionic charge or isoelectric point (pI) at a given pH. Ion exchange columns may be packed with positively charged beads (for anion exchangers) or negatively charged beads (for cation exchangers) that make up the support matrix. The charge density and pI of the molecules will determine the ionic capacity of the support matrix that is suitable for separating the molecules.

Ion exchange operations may be run using two different mobile phases or buffers (i.e., under gradient conditions). The starting buffer may be a low salt or ionic concentration buffer. The eluting buffer may have a significantly higher ionic concentration than the starting buffer. The operating pH can be determined by sample solubility and support matrix stability. For example, an ion exchanger may be run at a pH of about 6–11 and a linear gradient developed between about 0.3 and 1.0M NaCl. Water miscible organic solvents (for example, acetonitrile) may be used to decrease retention time, but it is preferred that the use of organic solvents be avoided so that the storage of organic chemical waste is precluded.

In yet another embodiment, affinity chromatography is used to separate molecules on the basis of specific activity. Affinity chromatography can be accomplished on a number of different types of matrices. Affinity supports include those that are capable of covalently binding a molecule and those that contain a ligand linked to the support for purification of molecules recognizable by the ligand. The selectivity and binding characteristics of the affinity support will be determined by the molecules to be separated.

The conditions required to bind molecules to and elute molecules from an affinity column will vary for each particular molecule as well. Generally, affinity purification of a molecule can be accomplished with simple step gradients, involving binding with one buffer, the binding buffer, and releasing the molecule with another, the elution buffer. If the binding and elution characteristics of a molecule are unknown, it is useful to run linear gradients of increasing salt or pH to optimize the purification. A logical sequence of elution conditions is acid elution, base elution, or chaotropic agents. After the eluant is chosen, the elution conditions may be refined by optimizing concentration, time, and temperature.

In still another embodiment, hydrophobicity interaction chromatography is conducted to resolve molecules based on differences in their surface hydrophobicity. (Reversed phase chromatography generally exploits these same characteristics, but is less preferred because of the requirement for organic elution solvents.) Interactions between hydrophobic groups with hydrophobic ligands attached to a chromatographic matrix mediate this chemistry and make it particularly suitable for functioning in a desalting capacity. The type of matrix, the nature of the hydrophobic groups, and the conditions of absorption and elution may be tailored to suit the unique properties of the molecules involved.

Selection and use of any of the chromatography embodiments provided herein is well within the skill of artisans in this field. The chromatography methods can utilize silica and polymer based technology. These applications of chromatography are compatible with HPLC and FPLC systems. Elution curves can be recorded continuously or determined by investigating individual fractions, by, for example, UV absorbance, agarose gel electrophoresis, and other analytical methods.

Pool Fractions

Fractions containing product can be pooled to obtain a plasmid DNA pharmaceutical grade material.

Pharmaceutical Grade Plasmid DNA

Following the obtaining of a plasmid DNA pharmaceutical grade material, it can be diluted in formulation buffer, such lactated Ringer's injection vehicle or other innocuous buffered delivery vehicle, or it may be precipitated or concentrated and then brought up in formulation buffer using known techniques as will be recognized by those with skill in the art.

At this stage, a solution containing pharmaceutical grade plasmid DNA may be sterilized. Any of several sterilization techniques may be adapted. Based on a preferred embodiment, sterilization is achieved by filtration.

A filter material may be implemented that is characterized by pores having a diameter large enough to allow the filtrate to pass through efficiently but small enough so that the filter material retains air-borne microorganisms and the like introduced during processing. Accordingly pore sizes are preferably from about 0.01 to 10 microns, with a range of from about 0.1 to 1 micron particularly preferred. The material from which the filter is manufactured can be a synthetic material or an organic or inorganic natural material; however, it should tend not to bind plasmid DNA. Nor should it be inclined to restrict substances the are meant to flow through the filter along with the plasmid DNA, e.g., ingredients composing formulation buffers and such. Additionally, it should be non-pyrogenic. In a preferred embodiment, the filter material has an average pore size of about 0.2 µm. The filter is also, importantly, sterile.

Sterilization is advantageously conducted under aseptic conditions in a class 100 hood or equivalent. It is contemplated that plasmid DNA may be precipitated or concentrated either before or after sterile filtration and resuspended in a formulation buffer. It is additionally contemplated that, in conclusion, the final product may be filled into vials during aseptic processing, the vials sealed and labelled, and the drug product dispatched for therapeutic administration, for example, in in vivo or ex vivo gene therapy.

Particular aspects of the invention may be more readily understood by reference to the following examples, which are intended to exemplify the invention, without limiting its scope to the particular exemplified embodiments.

EXAMPLE 1. Description of VCL-1005

VCL-1005 consisted of plasmid DNA. (A plasmid map is attached as FIG. 1.) The plasmid DNA was derived from a pBR322 plasmid and encoded a human MHC gene, HLA-B7. The plasmid was produced by bacterial fermentation.

This covalently closed circular (predominately supercoiled) DNA macromolecule was biosynthesized in bacterial cells grown in a selection media requiring the expression of the kanamycin resistance protein encoded by a portion of the plasmid DNA. The DNA was subsequently purified from essentially all other cellular material. The plasmid was approximately 5000 bp in size, which resulted in a molecular weight of about $3\times10^6$ g.m.u.

In addition to the bacterially expressed gene encoding kanamycin resistance protein (Tn903), the plasmid DNA also encoded the heavy (human HLAB7 cDNA) and light (chimpanzee B-2 Microglobulin cDNA) proteins of a Class 1 Major Histocompatibility Complex, termed HLA-B7. These two proteins were expressed on a bi-cistronic mRNA. Eukaryotic cell transcription of this mRNA was dependent on a Rous Sarcoma Virus promoter sequence derived from the 3' Long Terminal Repeat and on a transcription termination/polyadenylation signal sequence derived from the bovine growth hormone gene. Eukaryotic cell expression of the heavy chain was regulated by the 5' cap-dependent protein translation start site. Expression of the light chain was regulated by a Cap Independent Translational Enhancer (CITE) sequence derived from the Encephalomyocarditis Virus. Finally, replication of the plasmid in bacterial cells was controlled by the presence of a bacterial origin of replication.

Individual preparations of purified plasmid DNA were characterized from concentration by optical density absorbance measurements using a spectrophotometer with a light source set at 260 nanometers (1 absorbance unit=50 µg of double-stranded DNA). Plasmid size and percentage of covalently closed circular product was determined by electrophoretic migration, relative to known standards, on agarose gels. Additional characterization was made using selective restriction endonuclease digestion of the plasmid DNA with subsequent separation and sizing of the predicted DNA fragments by agarose gel electrophoresis. Expression of the coding sequences was determined by growth of transformed bacterial cells in selection media (for kanamycin resistance)

and by a FAC antigen presentation assay of HLAB7 heavy and light chains on VCL1005 plasmid DNA DMRIE/DOPE transfected eukaryotic cells grown in in vitro cell culture.

EXAMPLE 2. Construction of VCL-1005

VCL-1005 was constructed using independent segments of DNA cloned into a high copy number bacterial plasmid DNA. The plasmid was designed so that its sequence would facilitate high levels of replication in bacterial cells, express a dominate selectable resistance protein during bacterial cell culture, and, when introduced into eukaryotic cells, effect a high level of expression of the two Class I MHC component proteins, HLA-B7 and B-2 Microglobulin. Each component was subcloned into the backbone plasmid using standard molecular biological procedures and commercially available restriction endonucleases and other DNA modification enzymes (i.e., E. coli (Klenow fragment) DNA polymerase, bacteriophage T7 DNA polymerase, bacteriophage T4 ligase, etc.). Subcloned products were tested for fidelity and orientation (where necessary) by both restriction endonuclease mapping and junctional DNA sequence analysis. The final DNA plasmid drug was completely sequenced on both strands of DNA. All subsequent references to domains of the VCL-1005 DNA are based on the first nucleotide derived from the RSV promoter, 5' end, being arbitrarily designated #1.

The backbone plasmid DNA was derived from pBR322, a vector widely used in molecular biology laboratories and whose origin of replication was taken from the naturally occurring bacterial plasmid, ColiE1 (Bolivar, R., et al., Gene 2:95–113 (1977)). The 952 bp fragment of pBR322 used in the VCL-1005 plasmid represented the region from pBR322 base number 2244 (Acc1 restriction endonuclease site; blunt ended) to base number 3193 (BspH1 restriction endonuclease site), using the unique EcoR1 restriction endonuclease site as pBR322 base 1. This backbone plasmid fragment was found between base number 4013 and 4965 of VCL 1005 DNA and comprised a bacterial origin of replication. It did not contain any open reading frames known to be expressed in either bacterial or animal cells.

Eukaryotic gene expression was regulated by the Avian Rous Sarcoma Virus (RSV) 3' Long Terminal Repeat (LTR) promoter sequence. This sequence was derived from the Schmidt-Ruppin strain of RSV (Swanstrom, R., et al., Proc. Nat. Acad. Sci., U.S.A. 78:124–128 (1981)) and was cloned by isolating DNA bounded by the Pvu II site at viral base number 8673 and the Bfa I site at viral base number 9146. The use of this promoter sequence to regulate the expression of heterologous genes in eukaryotic cells was described more than 10 years ago by Gorman, C., et al. (Proc. Nat. Acad. Sci., U.S.A. 79:6777–6781 (1982)). The RSV DNA fragment used in the construction of the VCL-1005 plasmid was taken from the pRSVβ-globin (Gorman, C., et al., Science 221:551–553 (1983)). Although this regulatory sequence was found in an avian retrovirus, this 3' LTR has been tested and shown to have no intrinsic oncogenic activity in either avian or mammalian cells (Westphal, C., et al., Cold Spring Harbor Symp. Quant. Biol. 50:411–416 (1985)) (Mahon, M., et al., Proc. Nat. Acad. Sci., U.S.A. 85:1165–1168 (1988)) (Overbeek, U., et al., Science 231:1574–1577 (1986)). The RSV LTR promoter domain in VCL-1005 represented base pairs 1 through 529. This included a 56 base pair region of chemically synthesized oligonucleotide DNA which modified this regulatory sequence to effect a higher level of eukaryotic cell expression of the down stream coding sequences. The oligonucleotide removed a polyadenylation signal sequence (i.e. AATAAA with TCTAGA, an Xba I restriction endonuclease site) originally found in the RSV DNA sequence. It also introduced a strong translational signal sequence (Kozak, M., et al., Nucleic Acids Res. 15:8125 (1987)) proximal to the translational initiating codon, ATG. Moreover, this synthetic oligonucleotide was also used to incorporate a number of restriction endonuclease sites (i.e., SalI, HindIII, and NcoI) to facilitate subcloning of both 5' and 3' DNA elements.

The Class 1 MHC coding sequences for human HLA-B7 and B 2 microglobulin proteins were located 3' to the RSV LTR described above. Eukaryotic transcription of a single, bi-cistronic mRNA molecule was regulated by the RSV promoter domain. Translation of this bi-cistronic mRNA was affected by both a CAP dependent and a CAP independent ribosome recognition sequence. The CAP independent signal was taken from the murine encephalomyocarditis (EMC) virus genome and was cloned between the HLA-B7 heavy and light chains.

EXAMPLE 3. Fermentation of VCL-1005

The fermentation process was performed as a 10-L batch fermentation in TB medium (complete, containing the antibiotic kanamycin) in a Braun fermenter.

a. Inoculum Preparation

Using a 0.1-ml frozen aliquot of E. coli strain DH10B glycerol stock containing the antibiotic kanamycin, a 2-L flask containing 1-L TB medium (complete) was inoculated. TB medium was prepared by adding 24-gm yeast extract and 12-gm Trypticase peptone to a 2-L shake flask. Then, 900-ml deionized water was added to the flask and mixed thoroughly. When all contents were in solution, 4-ml glycerol was added and mixed thoroughly. The flask was plugged and the plug covered with Sterigard paper. The flask was then autoclaved for 30 min. at not less than 121° C. When medium was cooled, 50-mg sterile kanamycin and 100-ml sterile phosphate solution were added. Phosphate solution was prepared by dissolving 12.5-gm $K_2HPO_4$ and 2.3-gm $KH_2PO_4$ in 100-ml deionized water in a 500-ml flask. The flask was plugged and the plug covered with Sterigard paper. The flask was then autoclaved for 30 min. at not less than 121° C. With the addition of the kanamycin and the phosphate solution, the TB medium was complete. The inoculated flask was shaken at 37° C. and 300–400 rpm for 10–20 hours in a shaker incubator cabinet.

b. Fermenter Preparation

The Braun Biostat ED fermenter was cleaned with a solution of sodium hydroxide, followed by a phosphoric-acid wash, then thoroughly rinsed with deionized water. The pH probe was calibrated by immersing it in pH 7.0 standard buffer, then in pH 4.0 standard buffer. Added to the fermenter was 6-L deionized water. Then, 240-gm yeast extract powder and 120-gm Trypticase peptone was added to the fermenter. The agitator was run to facilitate dissolving the powder. Next, 40-ml glycerol and 1.5-ml antifoam were added to the fermenter. The walls of the fermenter were rinsed with deionized water and the volume brought to 9-L. The contents of the fermenter were sterilized by using batch control automatic cycle, on control unit, for 30 min. at 121° C.

c. Fermentation Conditions

The fermenter was monitored using the following control loops: pH, dissolved oxygen (DO), and temperature. Temperature was controlled to 30° C., ±0.5°. Stirring speed was set for 600 rpm and the airflow control to 1 v/v/m, ±0.1 v/v/m, pH was 7.0±0.5.

d. Fermentation Inoculation

All control loops on the fermenter were verified to be on and operating correctly. A septum on the fermenter headplate was pierced with the sterilized manufacturer's inoculation fitting having 3, 3-ft to 4-ft, 3/32-ID silicone tubes attached. One sterile tube was used to introduce 1-L phosphate solution into the fermenter. A second sterile tube was used to introduce the inoculum into the fermenter. The third sterile tube was reserved for pH control, if necessary. All solutions were introduced into the fermenter using a peristaltic pump. Sterile kanamycin solution, 50-mg/ml, i.e., 500-mg/fermenter, was added to the phosphate solution.

e. Fermentation and Cell Harvesting

Fermentation proceeded with the above-listed parameters under automatic control. Samples of the fermentation broth were removed from the harvest valve at intervals, and the fermentation was complete when the OD600 was 20 or greater. Cells were harvested from the fermenter by drawing broth from the harvest valve into tared 1-L centrifuge bottles. Cells were concentrated by centrifugation at up to 4900 rpm for 30 min. The supernatant was decanted, and the bottles were weighed to determine cell yield.

EXAMPLE 4. Purification of VCL-1005

VCL-1005 was purified using the following protocol:

a. Cell Lysis

The cell paste was resuspended completely in 7 mls per gram wet bacterial weight Solution I (61 mM glucose+25 mM Tris buffer pH 8.0+10 mM EDTA pH 8.0) with a magnetic stirrer at room temperature. To this solution 14 mls per wet bacterial weight Solution II (0.2N NaOH+1% SDS) was added and swirled until a clear viscous solution appeared. This lysed cell solution was incubated on ice for 10 minutes without any additional swirling to prevent chromosomal DNA shearing. To the lysed cell solution 10.5 mls per wet bacterial weight of ice cold Solution III (3M potassium acetate, pH 5.0)) was added, inverted, shaken vigorously, and incubated on ice for 10 minutes.

b. Filtration

The lysate was carefully filtered through two layers of Miracloth® to remove the bacterial cell wall. This was repeated 3 additional times through 16 layers Miracloth® each passage. Crude DNA filtrate was precipitated with 0.6 volumes cold (approximately −20° C.) isopropanol, adding about 200 mls at a time and swirling, and incubated for 1–2 hours at room temperature. The crude nucleic acid precipitate was collected by centrifugation at 12000 rpm for 30 minutes at 5° C. After discarding the supernatant, the pellet was drained for 15 minutes and then was uprighted to air dry for 5 minutes. The DNA pellet was resuspended completely in TE buffer (0.01M Tris-base+0.001M EDTA pH 8.0) using approximately 1 ml TE buffer per original wet weight bacteria.

c. RNA and Lipopolysaccharide Removal

After the pellet was resuspended in TE buffer as described above, 0.29 grams per original wet weight bacteria of ammonium acetate was dissolved into the DNA/TE resuspension so that the final concentration was 2.5M. Additional TE buffer was added if necessary to correct the volume. This mixture was incubated on ice for 15 minutes and then the process was continued or it was transferred to 4° C. overnight.

The mixture was centrifuged at 10,000 rpm for 20 minutes. The supernatant was filtered through a 0.8μ membrane and then an equal amount of phenol:chloroform:isoamyl alcohol (25:24:1) was added. This phenol, etc., combination was stirred using a magnetic stirrer for 30 minutes at room temperature. The combination was briefly centrifuged at 5000 rpm to facilitate the separation of the aqueous and organic phases. The upper, aqueous phase was collected and the DNA precipitated by the addition of 2 volumes −20° C. ethanol, mixed and incubated at −20° C. for a minimum of 1 hour or overnight.

The precipitate-containing material was centrifuged at 12,000 rpm for 30 minutes. The supernatant was discarded and the remaining pellet was allowed to drain for 15 minutes and then uprighted to air dry for 5 minutes. The pellet was resuspended in TE buffer using 0.5 mls per original wet weight bacteria.

Sodium acetate at pH 5.2 was added to the resuspended pellet to a final concentration of 1.1M. 30% PEG in 1.6M NaCl was added to this solution so that the final concentration was 4% PEG. This PEG-containing material was allowed to incubate at 4° C. for a minimum of 8 hours.

d. Final DNA Precipitation

Following the 4% PEG precipitation, the material was centrifuged at 12,000 rpm for 30 minutes. The supernatant was decanted to a clean bottle and additional 30% PEG in 1.6M NaCl was added so that the final concentration of PEG was 10%. This PEG-containing material was incubated at 4° C. for a minimum of 8 hours. It is then centrifuged as described above. The pellet was drained and then resuspended in a small volume (<10 mls) of TE buffer. One-tenth volume of 3M sodium acetate pH 5.2 was added and then 2 volumes of cold (approximately −20° C.) ethanol were added. This mixture was incubated at −20° for a minimum of 1 hour. It was centrifuged at 12,000 rpm at 4° C. for 30 minutes and resuspended in a small amount of column buffer (see below for details).

e. Gel Filtration Chromatography

A Pharmacia S-1000 (Pharmacia, Piscataway, N.J.) size exclusion tandem column was poured in two Pharmacia XK26/100 columns (Pharmacia, Piscataway, N.J.) with a final bed height of 80–85 cm (2.6×80 cm) each resulting in a total column volume of approximately 900 mls. The columns were individually pressure packed in one direction, reversed and connected in series for equilibration and operation. The column was equilibrated in TE+150 mM NaCl, pH 8.0, and run at a flow rate of 0.75 mls/min. or 17 cm/hr.

Partially purified plasmid DNA dissolved in the above buffer at less than 1% of the total column volume was filtered over a 0.22 micron sterile non-pyrogenic syringe filter and loaded on the column. Column operation and fraction collection was automated with a Pharmacia FPLC (Pharmacia, Piscataway, N.J.).

Product (super coiled monomer) began elution at 0.3 to 0.4 column volumes immediately following and slightly overlapping dimer. Product completed elution at 0.5 to 0.6 column volumes depending upon the overall load to the column.

Fractions (approximately 0.5–1% of column volume) were collected over the product elution zone and analyzed by 0.8% agarose gels. The exact range of product elution was determined from the gel analysis. Appropriate fractions were pooled and precipitated with 2 volumes of cold ethanol overnight at −20° C.

The ethanol precipitated fractions were spun at 12,000 rpm for 30 minutes at 4° C. The pellets were drained in a laminar flow hood for 15 minutes, inverted and air dried for 5 minutes. The pellet was resuspended in lactated Ringer's for Injection USP such that the final concentration was approximately 1 mg/ml. This constituted plasmid DNA pharmaceutical grade material. A sample was given to QC and the remainder was either stored or the concentration adjusted for dosage and sterile fill.

Following chromatography, the column and FPLC were sanitized with one column volume of 0.1M NaOH.

EXAMPLE 5. Production of Plasmid Enriched Crude Lysate Without the Use of Reagents Not Generally Recognized as Safe To 200 grams of wet cell paste, 600 mls of 0.2 M sodium acetate, pH 8.2, was added. This blend was gently mixed for about 5 to 10 mins to yield a homogeneous cell suspension. To the homogeneous cell suspension was added 500 mls of a 0.2M sodium hydroxide and 1% Tween® 80 (W/V) solution. This suspension was gently mixed for about 5–10 minutes to obtain a lysate. Deionized $H_2O$ was added to the lysate to a volume of 2000 mls. Glacial acetic acid was then added to a pH of 5.0. Cell debris was subsequently removed by filtration. To the filtrate, 1200 mls of cold (approximately −20° C.) 2-propanol was added to yield a plasmid enriched partially purified DNA precipitate.

EXAMPLE 6. Production of Partially Purified DNA Enriched with Plasmid Without Using Alcohols or Centrifugation a. Cell Lysis First, 200 grams (wet weight) of *E. coli* cells were thawed overnight at approximately 4°–8° C. The thawed biomass was transferred to a 10 liter carboy. Then 1.4 liters of solution I with 0.05M EDTA was added and the cells mixed until homogeneous. (Solution I=0.025M Tris-Base, 0.061M Glucose, pH 8.0).

Next, 2.8 liters of solution II with an 0.05M EDTA was added to cells in the carboy. The resulting suspension was mixed by repeated inversion of the carboy. The carboy was set in wet ice for 10 minutes. (Solution II=1% SDS, 0.2M NaOH).

Then, 2.1 liters of solution III with 0.05M EDTA (kept chilled at 4°–8° C. prior to addition) was added and the resulting solution mixed by repeated inversion of the carboy until the flocculent material was uniformly distributed. The carboy was returned to the wet ice for 10 minutes. (Solution III=3.0M K Acetate, pH 5.0).

b. Filtration

The lysate was poured through two layers of Miracloth® in a Buchner funnel apparatus to remove the large debris. This was repeated 2 additional times through 16 layers Miracloth® each passage. The final volume of the crude filtrate was 5.05 liters.

c. Plasmid DNA Precipitation with PEG-8000

Next, 600 grams of PEG-8000 was added to the crude filtrate with stirring. The volume was brought to 6.0 liters with 0.01M Tris-Base, 0.05M EDTA, 1.6 NaCl, pH 8.0. Final pH of the solution was not determined. This brought the final concentration of PEG-8000 to 10% (w/v). The glass carboy was transferred to 4°–8° C. and allowed to stir overnight.

d. Filtration of the Plasmid DNA

After incubating overnight, 120 grams (20 gram/liter) of analytical grade Celite® filtering aid (Celite Corp., Lompoc, Calif.) (diatomaceous silica) was added to the 10% PEG-8000 plasmid DNA precipitate and stirring continued at room temperature. While this was mixing, a ten inch Buchner funnel was set up with a wide mesh polypropylene screen approximately 8 inches in diameter covered by a Whatman No. 1 equivalent 10 inches in diameter filter. This was precoated with approximately 1 cm of Celite® applied in TE buffer. Following application of the precoat, the 6 liters of 10% PEG-8000 partially purified DNA precipitate was applied to the Buchner apparatus with suction. Following the filtration, suction was continued until the Celite® cake containing the plasmid DNA precipitate was relatively dry (10 minutes).

e. Recovery of Plasmid DNA Precipitate

The Celite® cake was removed and suspended in 1 liter of 0.01M Tris-Base, 0.05M EDTA, pH 8.0, with stirring for 90 minutes. This step dissolved the plasmid DNA precipitate collected on the cake. Ammonium acetate was added to the suspended cake to a final concentration of approximately 2.5M. Stirring was continued for 30 minutes at approximately 4°–8° C. The volume at this point was 1.5 liters. The ammonium acetate precipitated a portion of the lipopolysaccharide and RNA impurities. The resulting slurry was filtered once again on Buchner apparatus with a Whatman No. 1 equivalent filter exactly as described above. In this step the ammonium acetate precipitated impurities were captured in the Celite® cake and the plasmid DNA passed through into the filtrate.

f. Final Purification of Plasmid DNA (At this point in the experiment, it was decided to concentrate the plasmid DNA filtrate by a 2-propanol precipitation in order to load the material on a Pharmacia S-1000 column (Pharmacia, Piscataway, N.J.) as soon as possible to determine the yield and spectrum of impurities. In practice, the plasmid DNA would be concentrated by anion exchange, ultrafiltration, or a second PEG-8000 precipitation.)

In this step, 1.5 liters of filtrate was recovered from step e. Residual Celite® was removed from the filtrate passing it sequentially over a Whatman No. 1 equivalent followed by a 0.8 micron nitrocellulose membrane.

Then, 0.9 liters of cold (approximately −20° C.) 2-propanol was added to the final filtrate and the resulting solution placed in a −20° C. freezer for 1 hour. The precipitated DNA was collected by centrifuging in a Sorvall RC3 at 9000 rpm for 45 minutes at 4° C. The supernatant was discarded, the pellets drained and then air dried for approximately 15 minutes. The pellets comprising approximately one third of the plasmid DNA recovered were dissolved in 5 ml of 0.01M Tris-Base, 0.01M EDTA, 0.15M NaCl, pH 8.0.

This sample was applied directly to a tandem (2.6 cm×100 cm) Pharmacia S-1000 column (total column volume=900 ml) (Pharmacia, Piscataway, N.J.) that was previously equilibrated in 0.01M Tris-Base, 0.01M EDTA, 0.15M NaCl, pH 8.0. The column was run at a flow rate of 0.75 mls/m 17 cm/hr.

Next, 5 ml fractions were collected starting at 250 ml elution volume through 650 ml. The fractions were analyzed by standard 0.8% agarose gels and fractions 28–40 pooled as predominantly monomeric supercoiled plasmid DNA. Final yield was determined to be 2.1 mg of greater than 95% closed circular DNA.

These steps were repeated for the remaining plasmid concentrate and 2.4 mgs and 3.16 mgs were recovered bringing the total recovery to 7.56 mgs.

EXAMPLE 7. Use of PEG-8000 to Replace Organic Extraction With Phenol:Chloroform:Isoamyl Alcohol and Similar Organic Extractors Differential PEG precipitation was ascertained to replace organic extraction and other purification systems in terms of optimal recovery of plasmid DNA and minimal retention of contaminants to produce a superior partially purified plasmid DNA product.

a. PEG-8000 Titration

Several levels of PEG-8000 were explored to determine the approximate concentration that would precipitate plasmid DNA.

A cleared lysate produced following filtration after Solution III, as described in Example 6 above, was the starting material for this experiment. The experimental control was treated with 0.7 volumes of −20° C. 2-propanol. A 30% stock solution of PEG-8000 containing 1.6M NaCl was prepared and added to the crude lysate to produce the final PEG concentrations shown in the table below.

| Treatment Group | Vol. Cell Lyzate |
|---|---|
| 1. IPA Control - 0.7 × Vol. | 100 ml |
| 2. 5% PEG 8000 | 100 ml |
| 3. 7.5% PEG 8000 | 100 ml |
| 4. 10% PEG 8000 | 100 ml |
| 5. 12.5% PEG 8000 | 100 ml |

The resulting solutions were mixed well and placed in a 10° C. water bath overnight. The solutions were then centrifuged for 40 minutes in a Sorvall RC3 using a GSA rotor at 10,000 rpm. The bottles were drained and the pellets resuspended in 5 ml of TE+0.7M NaCl. One ml of the plasmid DNA solution was then reprecipitated for 2 hours at −70° C. with two volumes of ethanol. (This was done simply as a sample preparation step for analysis by 0.8% agarose gels. Residual PEG in the sample can cause the DNA to streak on the gel.) The nucleic acid concentration was estimated by measuring the UV absorbance at 260 nm and the results are shown below.

| Treatment Group | A260/ml | Tot. A260 from 100 ml |
|---|---|---|
| 1. IPA Control - 0.7 × Vol. | 0.45239 | 228.46 |
| 2. 5% PEG 8000 | 0.0921 | 46.51 |
| 3. 7.5% PEG 8000 | 0.14294 | 72.18 |
| 4. 10% PEG 8000 | 0.17007 | 85.89 |
| 5. 12.5% PEG 8000 | 0.1505 | 76.00 |

The gels demonstrated that only a small amount of monomeric plasmid was precipitated at 5% PEG-8000. Higher molecular weight contaminants, however, were preferentially precipitated at the lower PEG concentration. By 10% PEG, plasmid was fully precipitated. These results were especially meaningful when placed in context with the A260 readings.

Significantly more absorbing material (~3×) was precipitated by the standard 2-propanol method than with PEG. Yet both were observed to precipitate the same amount of product (supercoiled plasmid) based on the agarose gel experiments. The data establish that PEG brings down product as effectively as alcohol, without precipitating out other impurities.

b. PEG-8000 Cuts

A series of PEG cuts were performed to exploit the property to advantage that higher molecular weight DNAs preferentially precipitate at lower concentrations of PEG.

Partially purified DNA was precipitated from 1000 ml of lysate with 0.7 volumes of −20° C. 2-propanol for 2 hours at −70° C. The solution was then centrifuged for 40 minutes in a Sorvall RC3 using a GSA rotor at 10,000 rpm. The resulting pellets were drained and air dried. Then the pellets were dissolved in TE buffer and pooled together. Ten ml was removed as a 2-propanol control. The rest of the material was made 1.11M sodium acetate and divided equally into 4×50 ml conical tubes (~10 ml each). Next, 30% PEG in 1.6M NaCl was added to each tube resulting in PEG-8000 concentrations of 3%, 4%, 5% and 6% PEG-8000. After mixing, the materials were allowed to incubate in a 10° C. waterbath overnight. The pellets were drained and then dissolved in 5 ml TE buffer and 10 microliters removed for agarose gel analysis. The remaining material, that is, the supernatant, was made 1.11M sodium acetate and all the volumes adjusted to 10 ml. The A260 readings that were observed are shown in the table following this section.

In the next step, 30% PEG in 1.6M NaCl was added to each supernatant-containing tube resulting in a final PEG-8000 concentration of 10%. After mixing, the contents were allowed to incubate in a 10° C. waterbath overnight. The resulting pellets were collected by centrifugation and dissolved in 10 ml of TE buffer. The A260 readings that were obtained are shown below.

| Sample | Volumn (ml) | 100 × Dil. A260 | A260/ml | Total A260 |
|---|---|---|---|---|
| 3% Peg 8000 Pellet | 10.00 | 1.0043 | 101.43 | 1014 |
| 4% Peg 8000 Pellet | 10.00 | 1.0226 | 103.28 | 1033 |
| 5% Peg 8000 Pellet | 10.00 | 0.91103 | 92.01 | 920 |
| 6% Peg 8000 Pellet | 10.00 | 0.85074 | 85.92 | 859 |
| 10/3% Peg 8000 Cut | 10.00 | 0.39519 | 39.91 | 399 |
| 10/4% Peg 8000 Cut | 10.00 | 0.21042 | 21.25 | 213 |
| 10/5% Peg 8000 Cut | 10.00 | 0.09091 | 9.18 | 92 |
| 10/6% Peg 8000 Cut | 10.00 | 0.08112 | 8.19 | 82 |
| IPA Control | 10.00 | 1.109 | 112.01 | 1120 |

Samples of all of the treatments were then analyzed on a 0.8% agarose gel.

The agarose gel analysis demonstrated that 3% PEG brought down nicked plasmid but not product. Also, 4% PEG was observed to precipitate nicked plasmid and a high molecular weight DNA. Both PEG concentrations brought down a significant amount of contaminating RNA. By 5% PEG, significant amounts of product were being precipitated. From these results it was concluded that a 4% PEG cut followed by a 10% PEG cut would result in the best yield of the highest quality product.

EXAMPLE 8. Size Exclusion Separation of Different Forms of DNA and Separation of RNA, Chromosomal DNA, and Protein from Plasmid DNA Size exclusion chromatography was established to result in superior separation of host contaminants and plasmid DNA species.

a. Initial Experiment

Pharmacia S-1000 size exclusion medium having a DNA exclusion limit of 20,000 base pair (Pharmacia, Piscataway, N.J.) was poured in a Pharmacia XK26/100 column (Pharmacia, Piscataway, N.J.) with a final bed height of 80 cm (2.6×80 cm) resulting in a total column volume of 425 mls. The column was pressure packed in one direction and reversed for equilibration and operation. The column was equilibrated in TE and 150 mM NaCl, pH 8.0, and run at a flow rate of 1.5 mls/min or 17 cm/hr.

Plasmid DNA was prepared using 200 g's of cell paste. The DNA was concentrated by ethanol precipitation, the sample was dissolved in 10 mls TE and 150 mM NaCl, pH 8.0, and loaded (1.1% bed volume) on the column.

Four peaks were resolved and analyzed by the standard agarose gel method. Peak 1 was chromosomal, peak 2 was a mixture of dimer and supercoiled, peak 3 was RNA and peak 4 appeared to be protein since nothing was visualized on the gel and the A260:A280 ratio was 1.3.

b. Process Integration of PEG Precipitation and S-1000 Size Exclusion Chromatography A side by side evaluation of the standard protocol with three process variations incorporating the 4% PEG precipitation and the S-1000 size exclusion column was conducted. First, 189 grams of cell paste was processed through the ammonium acetate step, as described in Example 4 supra, before dividing the material into the experimental groups. The basic differences in the four treatments are set forth in the table below.

| Treatment Group | Variables |
| --- | --- |
| I | Control - Standard method |
| II | 4% PEG Ppt + RNase + PK + No Phenol |
| III | 4% PEG Ppt + RNase + PK + Phenol |
| IV | 4% PEG Ppt + No Enzymes + No Phenol |

The experiments confirmed that with the use of a 4/10 PEG 8000 cut (4% PEG Ppt), phenol/chloroform extraction (phenol), Proteinase K (PK), and RNase could be eliminated.

Following the above treatments, the material was passed over Q Sepharose HP column, an anion exchanger, (Pharmacia, Piscataway, N.J.) by standard chromatographic methods.

The precipitated plasmid from the Q column was dissolved in TE+0.15M NaCL and fractionated over the S-1000 column. The columns were run at 0.75 ml/min in TE+0.15M NaCl. The S-1000 profiles from these experiments verified that Treatment Group IV was as effective as Treatment Groups I–III. That is, by employing a 4/10 PEG 8000 cut, organic extraction and treatment with the animal enzymes RNase and Proteinase K were found to be superfluous. Also, the implementation of the S-1000 column was observed, in all cases, to result in the fine resolution of chromosomal DNA, dimer and supercoiled plasmid, RNA and protein.

Agarose gel electrophoresis corroborated these results. A small variation in the separation of dimer and supercoiled plasmid was noted upon analysis of the four treatment groups, with Treatment Groups I and III yielding more dimer than Treatment Groups II and IV. It was clear that the 4/10 PEG 8000 cut was superior based on the requirement in the other methods for organic extraction and Proteinase K and RNase treatment to obtain the same level of purification. Also evident was the substantial fractionation that was accomplished by use of the S-1000 column. Endotoxin and Southern blot analyses substantiated these findings as well.

EXAMPLE 9. Tandem Size Exclusion Columns Separating Different Forms of DNA

Plasmid DNA was prepared, as described in Example 8 above, and applied to a tandem size exclusion column comprised of two Pharmacia XK26/100 columns (Pharmacia, Piscataway, N.J.) filled with Pharmacia S-1000 size exclusion medium (Pharmacia, Piscataway, N.J.) resulting in a total tandem column volume of approximately 900 mls. Resolution of different forms of DNA was enhanced by the increased separation capacity of the columns connected in series.

EXAMPLE 10. Ion Exchange Separation of Different Forms of DNA and Separation of RNA from Plasmid DNA In this particular example, an anion exchange medium Q Sepharose HP (Pharmacia, Piscataway, N.J.) was the stationary phase. Separation was accomplished developing a gradient between 0.7M and 0.9M NaCl in Tris Buffer with EDTA at pH 8.0. The load was prepared by standard laboratory methods described here. RNA passed directly through the column while different forms of DNA (nicked plasmid, supercoiled DNA) were separated by the salt gradient.

EXAMPLE 11. Endotoxin Removal by Size Exclusion Chromatography

Plasmid DNA was fractionated via size exclusion chromatography as described Example 8 above. Endotoxin concentration in the sample load was approximately 300,0000 EU/mg of plasmid DNA as measured by LAL. Endotoxin concentration in the plasmid pool was approximately 30–100 EU/mg of plasmid DNA.

EXAMPLE 12. Potency of Plasmid DNA Product Produced by Pharmaceutical Manufacturing Method Potency of VCL-1005 plasmid DNA purified by the pharmaceutical manufacturing method described herein was determined by HLA-B7 gene expression in HALL cells (a human melanoma cell line) following lipid-mediated in vitro transfection using DMRIE/DOPE. A working reference of VCL-1005 purified by a similar process was used as a positive control and to determine the relative potency of the test sample.

From 200,000 to 400,000 HALL cells were seeded per well into a 6-well plate the day before transfection. Cells were approximately 80–90% confluent monolayer prior to transfection. The DNA was dilute to 10 µg/ml and the DMRIE/DOPE was diluted to 20 µg/ml in a serum reduced medium like Opti-MEM. They were then combined in one polystyrene tube to form a complex for transfection. The cells were transfected with 1 ml of the complex (5 µg DNA, 5 µg DMRIE, 5 µg DOPE) per well in duplicate or triplicate. Cells were incubated at 37° C., 5% $CO_2$. Fresh medium and fetal calf serum were supplemented to the cells 1–4 hours and 24 hours post-transfection. Cells were harvested 48 hours post-transfection. HLA-B7 gene expression on the cell surface was labelled with anti-HLA-B7, followed by a fluorescent secondary antibody (anti-mouse IgG monoclonal antibody R-phycoerrythin conjugate). Immunofluorescent staining of the cells was analyzed by flow cytometry.

An increase in the mean fluorescence intensity was noted on transfected cells in contrast to the negative control (non-transfected cells or transfected with irrelevant gene). The test material was present at least two fold increase in mean fluorescence intensity over the negative control in terms of mean fluorescence intensity, and the relative potency was ½ to 2 fold (50%–200%) of the reference lot.

EXAMPLE 13. Manufacturing Process for Pharmaceutical Plasmid DNA from Plasmid DNA Pharmaceutical Grade Substance Through Sterile Fill See Example 4a–e supra. This example continues the process from plasmid DNA pharmaceutical grade material as follows:

Starting material was plasmid DNA pharmaceutical grade solution at 1 mg/ml or other appropriately determined concentration in lactated Ringer's for Injection USP or other innocuous buffered delivery vehicle. The plasmid DNA solution was filtered through a 0.2 micron sterile filter or equivalent in a class 100 biosafety area. The filtrate was collected in a sterile, pyrogen free container. In the class 100 area, 0.35 ml of sterile plasmid DNA solution or other appropriate amount were aliquoted in pyrogen free, sterile type I borosilicate glass vials. In this example, each vial contained 0.35 mg of DNA. The vials were packaged with sterile teflon coated gray butyl stoppers and flip-off aluminum seals. The seals were crimped to complete sealing. The vials were then submitted to Quality Control and labeled appropriately.

EXAMPLE 14. Quality Specifications for Pharmaceutical Grade DNA

Plasmid VCL-1005 was transformed into a standard strain of DH10B *E. coli* (BRL, Gaithersburg, Md.). Cells were grown in a 10 L fermentor (Braun) using standard TB medium. At the end of the exponential phase, cells were harvested by centrifugation and lysed by alkaline lysis (without the use of lysozyme). Cell debris were separated by filtration. Plasmid DNA was precipitated and fractionated by standard low pressure chromatography. Appropriate fractions were pooled and the DNA was formulated. The concentration was adjusted and the DNA was sterile filtered and filled into sterile vials. Using the process of the invention, sufficient material was produced and purified for pre-clinical and clinical studies that met the criteria of identify, purity, potency and safety of pharmaceutical products derived from *E. coli* as defined by the FDA.

The quality control criteria that were satisfied rendering the product a pharmaceutical grade DNA are as follows:

In addition, acute and repeat-dose toxicity experiments in mice were conducted. Repeat-dose toxicity experiments on Cynomolgus monkeys were also conducted. No signs of acute toxicity nor signs of residual toxicity were observed.

EXAMPLE 15. Plasmid DNA Can Be Delivered Alone or In Combination with a Cationic Lipid Mixture Plasmid DNA purified by the pharmaceutical manufacturing method of the invention can be delivered alone into patients or in combination with a cationic lipid mixture. For example, the drug product is VCL-1005 plasmid DNA complexed with DMRIE/DOPE lipid mixture. Plasmid DNA and DMRIE/DOPE are formulated individually in separate containers. DMRIE/DOPE lipid vial is first reconstituted with lactated Ringer's injection vehicle and then combined with VCL-1005 plasmid DNA vial in the clinical setting prior to clinical use. Upon combination, the complex is delivered into patients for pharmaceutical application.

While particular embodiments of the invention have been described in detail, it will be apparent to those skilled in the art that these embodiments are exemplary rather than limiting, and the true scope of the invention is that defined within the attached claims.

What is claimed is:

1. A process for purifying plasmid DNA from host cell impurities (including host chromosomal DNA) to achieve a gene product adapted for clinical use comprising the steps of:

| VCL-1005 CHARACTERIZATION QUALITY CONTROL CRITERIA | | | |
|---|---|---|---|
| Test | Specification | Method | Detection Limit |
| Appearance | clear, colorless solution | visual observation | — |
| Total Size | approximates 4900 bp | agarose gel electrophoresis | — |
| Restriction Sites | approximates predicted bp: Bam HI 4900; Xho I/Xba I 1400, 3500; Bgl II/Xho I 1000, 1700, 2100 | agarose gel electrophoresis | — |
| Circular Plasmid DNA | >954 total nucleic acid | agarose gel electrophoresis | 0.01 µg |
| A260/A280 | 1.75 to 2.00 | UV absorbance | — |
| *E. coli* DNA | <0.01 µg/µg plasmid DNA | Southern slot blot | 100 pg |
| Protein | undetectable | BCA colorimetric assay | 1 µg |
| RNA | non-visualized on gel | agarose gel electrophoresis | 0.03 µg |
| Endotoxin | <0.1 EU/µg of plasmid DNA | Limulus Amebocyte Lysate (LAL) assay | 0.03 EU/ml |
| Pyrogenicity | not pyrogenic at 5 µg/kg rabbit body weight | rabbit pyrogen | 5 EU/kg |
| Sterility | no growth through 14 days | fluid thioglycollate | 1 cfu |
| Gene Expression | 50–200% expression as working reference | in vitro transfection/ fluorescence | 1 µg |
| General Safety | Pass | per 21 CFR 610.11 | — |

While the data established the removal of major host contaminants, it also demonstrated the separation of different forms of plasmid DNA, including concatemer plasmid DNA and monomer plasmid DNA.

(a) lysing host cells containing said plasmid DNA to obtain a lysate and subsequently treating with a salt to precipitate said host chromosomal DNA;

(b) clarifying said lysate to obtain a clarified lysate;

(c) adding a polyethylene glycol in sufficient quantity to said clarified lysate to obtain a precipitate of said plasmid DNA;

(d) collecting said precipitate;

(e) dissolving said precipitate to obtain a solution;

(e) adding a salt in sufficient quantity to said solution to precipitate said host cell impurities and to obtain a solute of said plasmid DNA; and (f) applying said solute to size exclusion or anion exchange chromatography to obtain said gene product adapted for clinical use;

wherein said process is conducted in the absence of lysozyme, RNase, Proteinase K, phenol, chloroform, and ethidium bromide.

2. A process for purifying plasmid DNA from host cell impurities (including host chromosomal DNA) to achieve a gene product adapted for clinical use comprising the steps of:

(a) lysing host cells containing said plasmid DNA in a base to obtain a lysate and subsequently treating with a salt and an acid to precipitate said host chromosomal DNA;

(b) clarifying said lysate to obtain a clarified lysate;

(c) adding a polyethylene glycol to about 10% to said clarified lysate to obtain a precipitate of said plasmid DNA;

(d) collecting said precipitate;

(e) dissolving said precipitate in a buffer to obtain a solution;

(e) adding ammonium acetate in sufficient quantity to said solution to precipitate said host cell impurities and to obtain a solute of said plasmid DNA; and (f) applying said solute to size exclusion or anion exchange chromatography to obtain said gene product adapted for clinical use;

wherein said process is conducted in the absence of lysozyme, RNase, Proteinase K, phenol, chloroform, and ethidium bromide.

3. A process for purifying plasmid DNA from host cell impurities to achieve a gene product adapted for clinical use comprising the steps of:

(a) lysing host cells containing said plasmid DNA to obtain a lysate;

(b) clarifying said lysate to obtain a clarified lysate;

(c) adding a precipitating agent in sufficient quantity to said clarified lysate to obtain a precipitate of said plasmid DNA;

(d) collecting said precipitate;

(e) dissolving said precipitate to obtain a solution;

(e) adding a precipitating agent in sufficient quantity to said solution to precipitate said host cell impurities and to obtain a solute of said plasmid DNA; and (f) applying said solute to size exclusion or anion exchange chromatography to obtain said gene product adapted for clinical use;

wherein said process is conducted in the absence of lysozyme, RNase, Proteinase K, phenol, chloroform, and ethidium bromide.

4. The process of any of claims 1, 2, or 3 wherein said process is further conducted in the absence of any added enzymes, organic extractants, and mutagenic reagents.

5. The process of any of claims 1, 2, or 3 wherein said process further comprises the step of:

(g) sterilizing, formulating, and vial filling said gene product.

6. The process of any of claims 1, 2, or 3 wherein the host cells are bacteria.

7. The process of any of claims 1, 2, or 3 wherein in step (b) said lysate is clarified by filtration through a diatomaceous silica filtering aid.

8. The process of any of claims 1, 2, or 3 wherein in step (f) said chromatography is size exclusion chromatography.

9. The process of claim 8 wherein said size exclusion chromatography comprises allowing said plasmid DNA-containing solute to contact with a size exclusion medium, having a DNA exclusion limit of about 20,000 base pair, at a pH of about 8.0, and a salt concentration of about 150 mM, and recovering plasmid DNA-enriched fractions.

10. The process of any of claims 1, 2, or 3 wherein in step (f) said chromatography is anion exchange chromatography.

11. The process of claim 10 wherein said anion exchange chromatography comprises allowing said plasmid DNA-containing solute to contact with an anion exchanger at a pH of about 8.0, developing a salt gradient between about 0.7M and about 0.9M, and recovering plasmid DNA-enriched fractions.

* * * * *

UNITED STATES PATENT AND TRADEMARK OFFICE
CERTIFICATE OF CORRECTION

PATENT NO. : 5,561,064
DATED : October 1, 1996
INVENTOR(S) : Marquet et al.

It is certified that error appears in the above-indentified patent and that said Letters Patent is hereby corrected as shown below:

```
Column 27, line 6, change "(e)" to --(f)--.

Column 27, line 9, change "(f)" to --(g)--.

Column 27, line 32, change "(e)" to --(f)--.

Column 27, line 35, change "(f)" to --(g)--.

Column 28, line 7, change "(e)" to --(f).

Column 28, line 10, change "(f)" to --(g)--.
```

Signed and Sealed this

Tenth Day of June, 1997

Attest:

Attesting Officer

BRUCE LEHMAN
Commissioner of Patents and Trademarks